US00PP21084P2

(12) United States Plant Patent
Thorup

(10) Patent No.: US PP21,084 P2
(45) Date of Patent: Jun. 22, 2010

(54) ***VIOLA* PLANT NAMED 'BALVIJAC'**

(50) Latin Name: *Viola cornuta*
Varietal Denomination: Balvijac

(75) Inventor: Troy Thorup, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 86 days.

(21) Appl. No.: 12/287,869

(22) Filed: Oct. 14, 2008

(51) Int. Cl.
*A01H 5/00* (2006.01)

(52) U.S. Cl. ..... Plt./323

(58) Field of Classification Search ..... Plt./323
See application file for complete search history.

(56) References Cited

OTHER PUBLICATIONS

Canadian PBR Application for 'Balvijac' available at http://www.inspection.gc.ca/english/plaveg/pbrpov/cropreport/vio/app00007201e.shtml accessed Mar. 4, 2010.*

UPOV ROM GTITM Computer Database, GTI Jouve Retrieval Software 2009/05 Citation for 'Balvijac'.*

* cited by examiner

*Primary Examiner*—Wendy C. Haas
(74) *Attorney, Agent, or Firm*—Audrey Charles

(57) ABSTRACT

A new and distinct cultivar of *Viola* plant named 'Balvijac', characterized by its lavender and yellow with a black blotch-colored flowers, medium green-colored foliage, and vigorous, trailing growth habit.

1 Drawing Sheet

Latin name of genus and species of plant claimed: *Viola cornuta.*

Variety denomination: 'Balvijac'.

BACKGROUND OF THE INVENTION

The present invention relates to a new and distinct cultivar of *Viola* plant botanically known as *Viola cornuta* and hereinafter referred to by the cultivar name 'Balvijac'.

The new cultivar originated in a controlled breeding program in Guadalupe, Calif. during November 2003. The objective of the breeding program was the development of *Viola* cultivars with high floriforousness, attractive flower coloration, medium green-colored foliage, and low to trailing growth habit.

The new *Viola* cultivar is the result of cross-pollination. The female (seed) parent of the new cultivar is the proprietary *Viola cornuta* breeding selection designated 5573, not patented, characterized by its white flower with black blotch-colored flowers, medium green-colored foliage, and vigorous, trailing growth habit. The male (pollen) parent of the new cultivar is the proprietary *Viola cornuta* breeding selection designated 5750-3, not patented, characterized by its blue with black blotch-colored flowers, medium green-colored foliage, and vigorous, trailing growth habit. The new cultivar was discovered and selected as a single flowering plant within the progeny of the above stated cross-pollination during November 2005 in a controlled environment at Guadalupe, Calif.

Asexual reproduction of the new cultivar by terminal stem cuttings since November 2005 at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balvijac' as a new and distinct cultivar of *Viola* plant:

1. Lavender and yellow with a black blotch-colored flowers;
2. Medium green-colored foliage; and
3. Vigorous, trailing growth habit.

Plants of the new cultivar differ from plants of the female parent primarily in flower color and from plants of the male parent primarily in flower color.

Of the many commercially available *Viola* cultivars, the most similar in comparison to the new cultivar is 'Blue Moon', U.S. Plant Patent Application Applied For. However, in side by side comparisons, plants of the new cultivar differ from plants of 'Blue Moon' in at least the following characteristics:

1. Plants of the new cultivar have a flower color different from plants of 'Blue Moon';
2. Plants of the new cultivar have smaller flowers than plants of 'Blue Moon';
3. Plants of the new cultivar have smaller leaves than plants of 'Blue Moon'; and
4. Plants of the new cultivar are wider and more trailing than plants of 'Blue Moon'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balvijac'. The plants were grown in 4.5 inch pots for 6 weeks in a greenhouse at West Chicago, Ill. Plants were given one pinch at transplant.

DETAILED BOTANICAL DESCRIPTION

Figure 1:
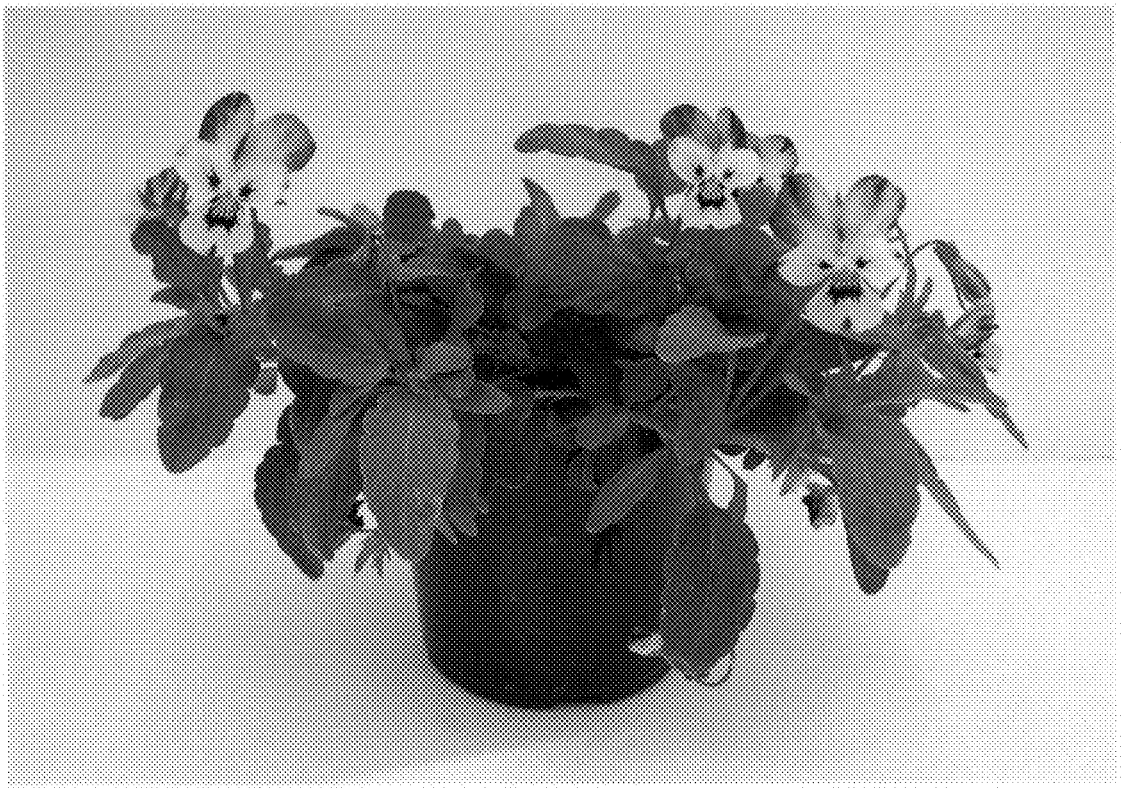
FIG. 1 illustrates a side view of the overall growth and flowering habit of 'Balvijac'.
Figure 2:
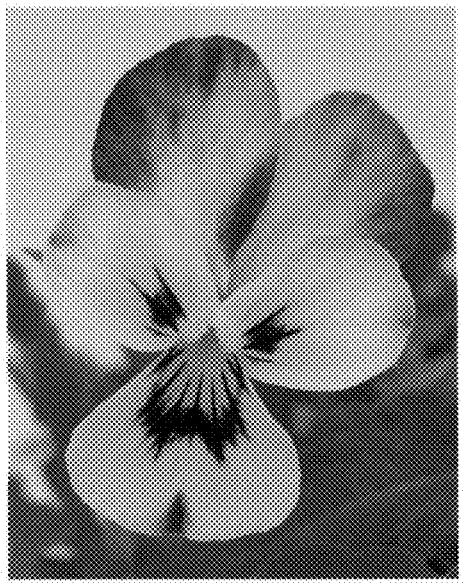
FIG. 2 illustrates a close-up view of an individual flower of 'Balvijac'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 17, 2008 between 9:00 a.m. and 11:00 a.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Viola cornuta* cultivar Balvijac.

Parentage:

*Female parent.*—Proprietary *Viola cornuta* breeding selection designated 5573, not patented.

*Male parent.*—Proprietary *Viola cornuta* breeding selection designated 5750-3, not patented.

Propagation:

*Type cutting.*—Terminal stem.

*Time to initiate roots.*—Approximately 5 to 7 days.

*Time to produce a rooted cutting.*—Approximately 24 to 28 days.

*Root description.*—Fine, fibrous.

*Rooting habit.*—Freely branching.

Plant description:

*Commercial crop time.*—Approximately 8 to 10 weeks from a rooted cutting to finish in a 10 cm pot.

*Growth habit and general appearance.*—Outwardly spreading, mounded, vigorous.

*Size.*—Height from soil level to top of plant plane: Approximately 8.0 cm. Width: Approximately 22.1 cm.

*Branching habit.*—Freely branching, pinching enhances branching. Quantity of main branches per plant: Approximately 6.

*Lateral branches.*—Strength: Strong, flexible. Length: Approximately 10.4 cm. Diameter: Approximately 3.0 mm. Length of central internode: Approximately 1.1 cm. Texture: Pubescent. Color of young and mature stems: 144A.

Foliage description:

*General description.*—Quantity of leaves per main branch: Approximately 9. Fragrance: None. Form: Simple. Arrangement: Alternate.

*Leaves.*—Aspect: Petiole is at an acute angle to stem and leaf blade is perpendicular to stem. Shape: Narrowly ovate. Margin: Crenate. Apex: Obtuse. Base: Rounded to truncate. Venation pattern: Pinnate. Length of mature leaf at center of stem: Approximately 4.2 cm. Width of mature leaf at center of stem: Approximately 2.0 cm. Texture of upper surface: Glabrous. Texture of lower surface: Pubescent venation. Color of upper surface of young foliage: 137C with venation 137B. Color of lower surface of young foliage: 138B with venation similar to lamina. Color of upper surface of mature foliage: Darker than 137A with venation 137B. Color of lower surface of mature foliage: Closest to 138A with venation similar to lamina.

*Petiole.*—Length: Approximately 2.1 cm. Diameter: Approximately 1.0 mm. Texture: Sparsely pubescent. Color: 144A.

*Stipules.*—Shape: Narrowly Ovate. Margin: Cleft. Apex: Obtuse. Base: Attenuate. Length: Approximately 3.0 cm. Width: Approximately 1.2 cm. Texture of upper surface: Glabrous. Texture of lower surface: Pubescent venation. Color of upper surface: 137A. Color of lower surface: 138B.

Flowering description:

*Flowering habit.*—'Balvijac' is freely flowering under outdoor growing conditions with substantially continuous blooming from spring through autumn and year-round in greenhouse environment.

*Lastingness of individual flower on the plant.*—Approximately 4 to 5 days.

Flower description:

*General description.*—Type: Single, zygomorphic, not persistent. Flower aspect: Pendant. Quantity per plant: Approximately 7. Fragrance: Sweet.

*Bud.*—Rate of opening: Generally takes 2 to 3 days for bud to progress from first color to fully open flower. Quantity showing color per plant: Approximately 4.

*Bud just before opening.*—Shape: Oblong. Length: Approximately 1.6 cm. Diameter: Approximately 5.0 mm. Color: 93A.

*Corolla.*—Shape: Orbicular, with a spur on lower petal. Length: Approximately 3.3 cm. Width: Approximately 2.7 cm. Depth: Approximately 5.3 mm.

*Petals.*—Quantity: 5. Shape of upper petals: Orbicular. Shape of lateral petals: Obovate. Shape of lower petal: Obcordate. Appearance: Velvety. Margin of all petals: Entire. Apex of upper and lateral petals: Obtuse. Apex of lower petal: Obcordate. Base of all petals: Attenuate. Length of upper petals: Approximately 1.8 cm. Width of upper petals: Approximately 1.5 cm. Length of lateral petals: Approximately 1.4 cm. Width of lateral petals: Approximately 1.1 cm. Length of lower petal: Approximately 1.4 cm. Width of lower petal: Approximately 1.6 cm. Texture of upper surface of all petals: Glabrous, with base of lateral petals densely glandular pubescent. Texture of lower surface of all petals: Glabrous. Color of upper surface of upper petals when first open: Irregular distribution of N89A, N89D, and 91D. Color of lower surface of upper petals when first and fully open: Irregular distribution of N89D, 91A, and 91D. Color of upper surface of lateral petals when first and fully open: 4B with streaks of 103A near base, margin of 91A fading toward center to 91D, occasionally a central spot on margin of N89A. Color of lower surface of lateral petals when first and fully open: 4D with margin of 91D. Color of upper surface of lower petal when first and fully open: Base of 6A with streaks of 103A, beyond the streaks 13A with a central spot on margin of 91A to N89B. Color of lower surface of lower petal when first and fully open: 4D with a central spot on margin of N89D.

*Spur.*—Quantity: 1 per flower on lower petal. Length: Approximately 7.0 mm. Diameter at proximal end: Approximately 2.0 mm. Diameter at distal end: Approximately 1.0 mm. Color: 4D with tip of 91A.

*Calyx.*—Shape: Stellate. Diameter: Approximately 2.4 cm.

*Sepals.*—Quantity per flower: 5. Shape: Lanceolate. Margin: Entire. Apex: Acute. Base: Rounded. Length: Approximately 1.9 cm. Width: Approximately 3.0 mm. Texture of upper and lower surfaces: Glabrous with pubescent margins. Color of upper and lower surfaces: 138A.

*Peduncle.*—Strength: Moderately strong. Aspect: Acute angle to stem. Length: Approximately 5.6 cm. Diameter: Approximately 1.5 mm. Texture: Glabrous. Color: 138B.

*Reproductive organs.*—Androecium: Stamen quantity: 5 per flower. Stamen arrangement: Tightly appressed against ovary. Stamen length: 3 mm. Two bear nectar spurs of 5 mm in length. Anther shape: Ellipsiodal. Anther length: Approximately 2.5 mm. Anther width: Approximately 1.5 mm. Anther color: 4C. Pollen amount: Moderate. Pollen color: 4D. Gynoecium: Pistil quantity: 1 per flower. Pistil length: Approximately 5.0 mm. Stigma shape: Globular. Stigma length: 1 mm. Stigma color: N144A. Style color: 144D. Ovary shape: Ovoid. Ovary position: Superior. Ovary length: 3 mm. Ovary width: 2 mm. Ovary color: 144C.

Seed and fruit production: Neither seed nor fruit production has been observed.

Disease and pest resistance: Resistance to pathogens and pests common to *Viola* has not been observed.

What is claimed is:

1. A new and distinct cultivar of *Viola* plant named 'Balvijac', substantially as herein shown and described.

* * * * *